US009925015B2

(12) United States Patent
Gravlee

(10) Patent No.: US 9,925,015 B2
(45) Date of Patent: Mar. 27, 2018

(54) WEARABLE PROTECTIVE ARTICLES DONNING SYSTEM

(71) Applicant: Thincubus, LLC, Fayette, AL (US)

(72) Inventor: Van Clark Gravlee, Fayette, AL (US)

(73) Assignee: Thincubus, LLC, Fayette, AL (US)

( * ) Notice: Subject to any disclaimer, the term of this patent is extended or adjusted under 35 U.S.C. 154(b) by 82 days.

(21) Appl. No.: 15/212,267

(22) Filed: Jul. 17, 2016

(65) Prior Publication Data

US 2017/0014198 A1 Jan. 19, 2017

Related U.S. Application Data

(60) Provisional application No. 62/194,048, filed on Jul. 17, 2015.

(51) Int. Cl.

| | |
|---|---|
| *A47G 25/90* | (2006.01) |
| *A61B 42/50* | (2016.01) |
| *A61B 42/40* | (2016.01) |

(52) U.S. Cl.

CPC .............. *A61B 42/50* (2016.02); *A47G 25/90* (2013.01); *A47G 25/904* (2013.01); *A61B 42/40* (2016.02)

(58) Field of Classification Search
CPC ..... A61B 42/40; A61B 42/50; A61B 17/3423; A47G 25/90; A47G 25/904; B25J 21/02; B65D 83/00
See application file for complete search history.

(56) References Cited

U.S. PATENT DOCUMENTS

| | | | | | |
|---|---|---|---|---|---|
| 1,938,685 | A | | 12/1933 | Breuls et al. | |
| 3,067,001 | A | * | 12/1962 | McCollum | A61B 42/50 128/898 |
| 3,481,101 | A | * | 12/1969 | Steadman | B65B 11/52 426/396 |
| 4,069,913 | A | * | 1/1978 | Harrigan | A61B 42/50 128/856 |
| 4,889,266 | A | * | 12/1989 | Wight | A61B 42/50 206/278 |

(Continued)

OTHER PUBLICATIONS

"Aeroglove," pp. 1-3, available at https://www.aeroglove.com, at least as early as Jul. 13, 2017.

(Continued)

*Primary Examiner* — Ismael Izaguirre
(74) *Attorney, Agent, or Firm* — Brinks Gilson & Lione

(57) ABSTRACT

An automated, manual or semi-automated donning system may be used to mechanically don wearable protective articles, such as gloves, without human contact with the outer surface of the wearable article. Thus, the system can be used to render wearable protective articles less capable of transferring disease organisms. In the donning system, a vacuum device can prepare a donning article for use in the donning system by inflating the article using negative pressure to the article's outer surface. Packaging of the wearable protective article may maintain sterility of the article and allow preparation of the article for donning without human contact. In addition, wearable protective articles used in the system may be subject to treatments to destroy potential pathogens. Alternatively, or in addition, a body part of the user may be subject to treatments to destroy potential pathogens during insertion into a wearable protective article prepared for donning by the system.

22 Claims, 7 Drawing Sheets

(56) References Cited

U.S. PATENT DOCUMENTS

| | | | |
|---|---|---|---|
| 4,909,413 A * | 3/1990 | McCutcheon | A47G 25/904 221/1 |
| 4,915,272 A | 4/1990 | Vlock | |
| 5,058,785 A * | 10/1991 | Rich | A47G 25/904 223/111 |
| 5,456,354 A | 10/1995 | Wood | |
| 6,193,117 B1 | 2/2001 | Poschelk | |
| 6,213,360 B1 * | 4/2001 | Aluisi | B25J 21/02 223/111 |
| 6,375,034 B1 | 4/2002 | Corbett | |
| 6,435,388 B1 | 8/2002 | Binder et al. | |
| 6,554,168 B2 | 4/2003 | Stobart | |
| 6,589,167 B1 * | 7/2003 | Shimomura | A61B 17/3423 128/897 |
| 6,932,253 B2 | 8/2005 | Sato | |
| 6,953,130 B2 | 10/2005 | Corbett | |
| 7,537,586 B2 | 5/2009 | Kline et al. | |
| 7,635,067 B1 | 12/2009 | Flynn | |
| 7,712,642 B2 | 5/2010 | Gaines et al. | |
| 8,479,918 B2 | 7/2013 | Howard | |
| 8,678,252 B2 | 3/2014 | Kelly et al. | |
| 8,807,402 B2 | 8/2014 | Backhaus et al. | |
| 9,283,444 B2 | 3/2016 | Cohen et al. | |
| 9,330,497 B2 | 5/2016 | Byrd et al. | |
| 2002/0113079 A1 | 8/2002 | Corbett | |
| 2004/0149788 A1 | 8/2004 | Sato | |
| 2006/0010563 A1 * | 1/2006 | Michel | A61B 42/50 2/159 |
| 2007/0170213 A1 | 7/2007 | Gaines et al. | |
| 2009/0307825 A1 | 12/2009 | Bhalla | |
| 2010/0147909 A1 | 6/2010 | Kelly et al. | |
| 2010/0263695 A1 * | 10/2010 | Hampe | B08B 3/041 134/113 |
| 2011/0186589 A1 * | 8/2011 | Lee | B65D 83/00 221/36 |
| 2011/0283439 A1 | 11/2011 | Backhaus et al. | |

OTHER PUBLICATIONS

"Delicatessen Glove Donning Machine Wins Capstone Contest," dated May 2014, pp. 1-4, available at https://mie.umass.edu/news/delicatessen-glove-donning-machine-wins-capstone-contest.

"How to Reload the AeroGlove Automated Glove Dispenser," dated May 28, 2015, pp. 1-2, available at https://www.youtube.com/watch?v=bT7PnvLE02A.

* cited by examiner

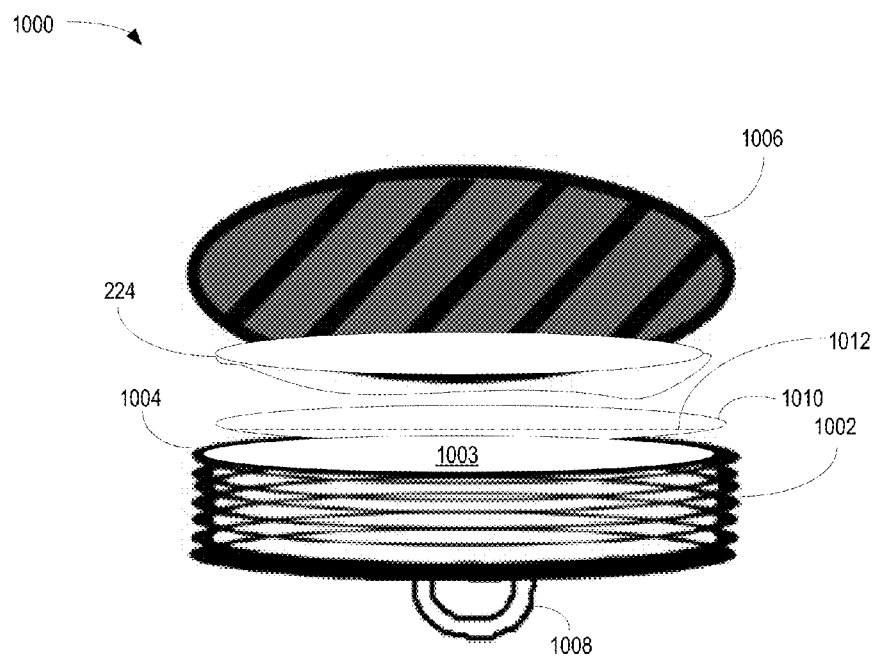
FIG. 10
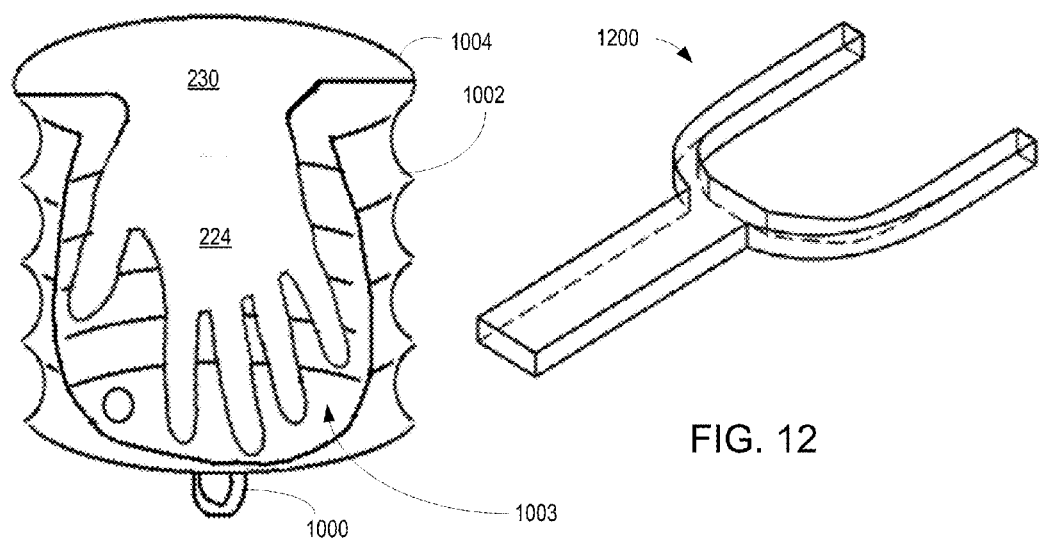
FIG. 11
FIG. 12

WEARABLE PROTECTIVE ARTICLES DONNING SYSTEM

TECHNICAL FIELD

This disclosure relates to donning of wearable protective articles, and more particularly to a system for the preparation of wearable protective articles for donning by a user.

BACKGROUND

The need to prevent pathogen transmission and to ensure personal protection has become a heightened focus of the healthcare industry in the wake of Zika, Ebola, MERS, HIV and other transmissible diseases. In agriculture, flu varieties threaten poultry, swine and other operations. In both settings, donning protective garments is time consuming. If improperly donned, the article can become contaminated. During the use of the garment there are opportunities for the garment itself to be a physical carrier of infection or disease.

BRIEF SUMMARY

This disclosure describes an automated, manual or partially automated donning system for preparing wearable protective articles, such as examination gloves, for donning by a user. The donning system may use a vacuum to open sanitary or sterile packaged articles, and then expand the wearable protective article to a size large enough to accommodate a body part of a user, or a portion of a human body. Processing of the packaged wearable protective articles by the donning system can include disinfecting activities. In some examples, the system can impart antimicrobial characteristics to the wearable protective article as part of the preparation for the donning process. In addition, in some examples, contact of the article with surfaces outside the sterile package may be avoided to maintain sterility.

In an example, the system may be a device specifically designed to accept gloves in individually sealed packaging, or a magazine of sealed packages, position those gloves for inflation, and inflate them in a common thumbs up orientation for either left or right hand. The device may treat the outer surface of the glove by photocatalysis of antimicrobials using exposure to a UV bulb, LED or flash. Alternatively or in addition, the system may treat the outer surface of the glove by exposure to a germicidal gas. Alternatively or in addition, the system may treat the outer surface of the glove by exposure to a germicidal mist or spray. Alternatively or in addition, the system may treat the outer surface of the glove by exposure to germicidal ozone. Alternatively or in addition, the system may treat the inside surface of the glove by spraying a lotion, gel or powder inside the glove for comfort, antimicrobial activity or both. Alternatively or in addition, the system may treat the hand as it is inserted by spraying a lotion or gel or powder onto it for comfort, antimicrobial activity, contamination indication or a combination of any of these.

The system may also include functionality such that opening and extending the packaging itself may inflate the glove. Also, in examples the system may accommodate long sleeve gloves, which may be treated as previously described. In addition, the system may be configured to accommodate footwear, such as booties, socks, stockings or boots. Further, the system may be configured to accommodate body wear such as pants, hose or waders as well as shirts and coats, protective hoods, and full body suits. Also, the system may be configured to accommodate condoms or condom catheters.

Other systems, methods, features and advantages will be, or will become, apparent to one with skill in the art upon examination of the following figures and detailed description. It is intended that all such additional systems, methods, features and advantages be included within this description, be within the scope of the invention, and the following claim.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

FIG. 10 is an exploded view of an example donning system.

FIG. 11 is a cutaway side view of an example donning system.

FIG. 12 is a perspective view of an example tool for the donning system of FIG. 10 or 11.

DETAILED DESCRIPTION

A donning system minimizes time lost in manually donning gloves and other wearable protective articles, such as garments or gear, by manipulating the article while still in the packaging as it transitions the article to an unpackaged and opened position in which the article is ready to receive a hand, foot or other body area to be inserted by the user. Wearable protective articles used with the donning system may be formed of any collapsible elastomeric material such that the article can be maintained in a compressed state and then expanded into an expanded state to receive a part of a body of a user. The donning system can inflate the glove or other article, such as by using a vacuum, and then allow the article to deflate while a body area is positioned therein, for a tight fit in seconds. In a contrasting example, the total time for a medical team to maintain a sterile field, while manually donning sterile surgical gloves, is many minutes per team member. The donning system may be used where sterile conditions are desired, such as in medical surgery and other medical situations. In alternatively, or in addition, the donning system may be used in clean or non-sterile applications such as clean room, food service, or other such applications where a controlled level of contamination by any undesired substance is desired. Thus, it should be understood that discussion of sterility throughout the disclosure may also be construed as meeting some other cleanliness or contamination standard depending on the application for which the wearable protective article will be used.

Figure 1:
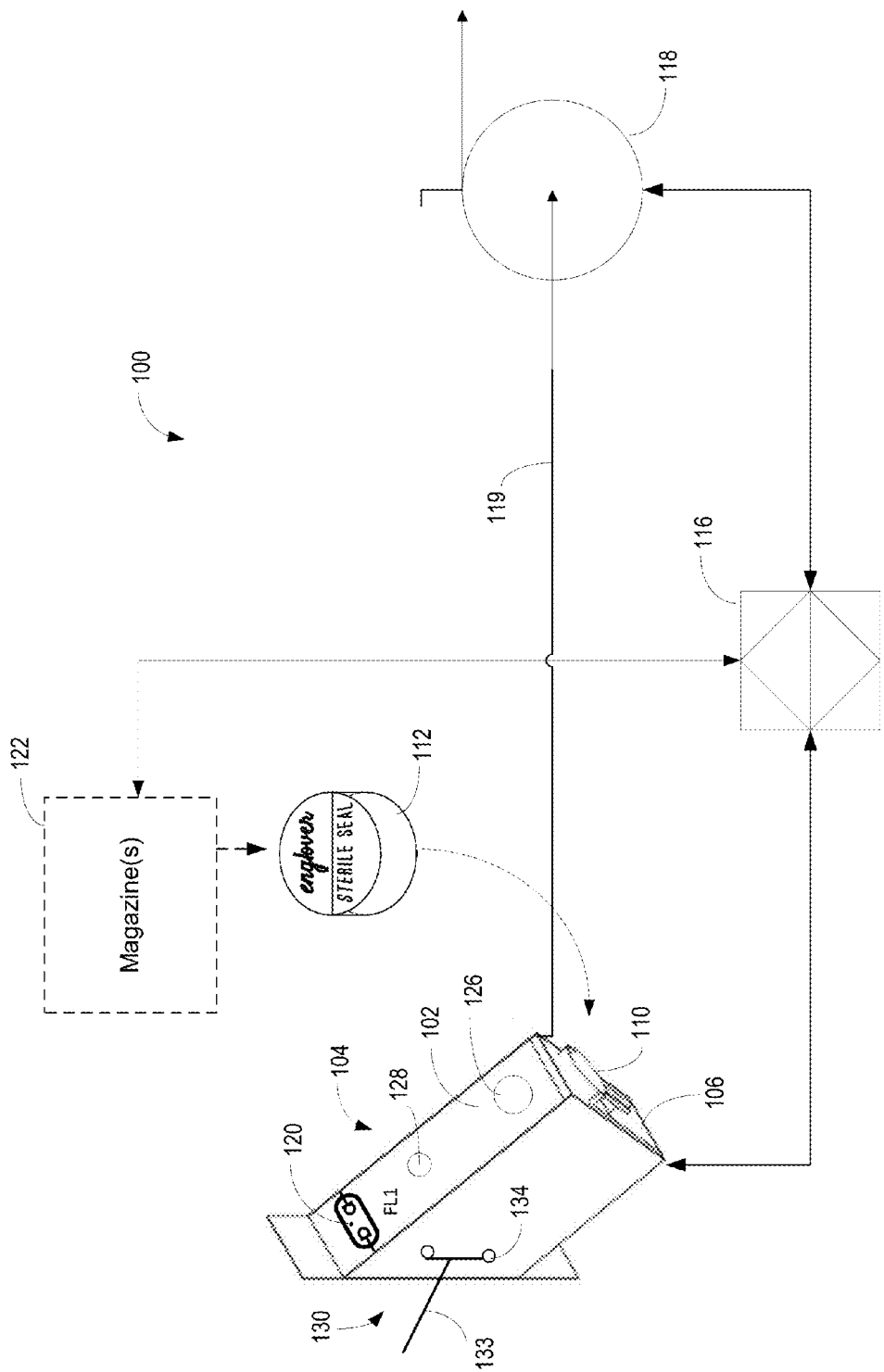
FIG. 1 is a functional diagram of an example of a donning system.

FIG. 1 is a functional diagram of an example of a donning system 100. The donning system 100 may include an enclosure 102 formed to include a vacuum chamber 104 therein. The enclosure 102 may include a package mount 106 forming a portion of the vacuum chamber 104. The package mount 106 may include a slidable member 110 configured to receive a sealed package 112. The sealed package 112 contains a wearable protective article that can be made ready for donning by the donning system 100. The sealed package 112 may be mounted on the package mount 106 manually by a user, using an automated mounting system, or some combination of manual and automated mounting. The donning system 100 may also include a processor 116 to provide the functionality and control of the system 100 as described herein. The vacuum chamber 104 may be supplied a vacuum by a vacuum source 118 via a vacuum line 119.

In example implementations, the donned articles can use titanium dioxide (TiO2) an ingredient common in many nitrile and latex glove formulations and easily added to others. TiO2 is mildly abiotic. When photo activated with a UV light source 120 that may be included in the system 100, the abiotic characteristic of TiO2 is greatly enhanced and is known to be effective to disrupt viral capsules and bacterial cell walls. Silver and silver ions share this photoactivated character with titanium but are even more deadly to virii and bacteria and can similarly be associated with articles. In addition, through experimentation it has been determined that silver nitrate (AgNO3) is an excellent coagulant for nitrile and can be part of the salt solution used to predip the forms of articles, before these forms of articles are dipped into the liquid elastomeric material from which the articles may be formed. In manufacturing some articles, such as elastomeric gloves, when removed from their forms, the side facing the form generally becomes the outside of the article, this will leave the salts or other abiotic compounds that are chosen as a predip additive on the outside of the article, such as on the exterior surface of the glove, not in contact with the wearer's skin, but where it can help reduce the environmental pathogens that the article could potentially come into contact with during use.

The donning system 100 provides an effective packaging and donning process, which can eliminate all human contact with the outside of the article during and even after the article is donned, to better ensure no contamination. After inflation and before the wearer places his body part in the article, such as a user's hand in an elastomeric glove, the donning system 100 can photoactivate all photoactive ions and compounds by exposing the external surface of the article to appropriate intensities and wavelengths of UV light from the UV light source 120.

In manufacture, certain nonpathenogenic bacteria can also contaminate the material from which an article is formed. For example articles formed with nitrile rubber can be contaminated with bacteria such as nitrilase bacteria which harms the integrity of the manufactured product. Although the FDA allows small amounts of antiseptics to be used in the formulation, with the donning system 100 the addition of antiseptic may be reduced and preferably eliminated. The formulations used in the donning system 100 and the use of the UV light source 120 in the donning process can accomplish this and also increase the shelf life of articles, such as non-sterile bulk gloves, while lessening the need for toxic materials, such as an antiseptic.

The donning system 100 can accept individually placed sealed packages 112 containing packaged articles, such as gloves. An automated magazine or magazines 122 can feed the sealed packages 112 to the package mount 106 as shown in FIG. 1. A scanning device 126 may be included in the system 100 to detect the size and/or shape of a user's body part. The processor 116 may use the detected information and the magazine 122 to load the appropriate size of glove based on the size of the body part, such as hands waved in front of the scanning device. Alternatively, a sealed package 112 of an appropriate size may be selected by a user and may be manually mounted on the package mount 106 by the user.

The donning system 100 may also include an inspection system 128, such as a camera or other visual inspection device or system. In an example, the inspection system 128 may be a three-dimensional machine vision system. The inspection capability may be used to confirm quality and integrity of the packaging and the wearable protective article, such as pinholes and striations or contaminants on the packaging or the article. In addition, the inspection capability may detect a size and/or shape of the body part of a user. Further, the inspection capability may provide operational information, such as confirmation of positioning of the packaging, positioning of a body part of the user in the article, or any other visual confirmation.

The donning system 100 may also include a treatment system 130 that includes a supply line 132 and ports 134. The treatment system 130 may provide treatments to destroy potential pathogens. The treatments may be delivered to the surface of a wearable protective article present in the vacuum chamber 104 via the supply line 132 and the ports 134. The ports 134 may be positioned at any location to penetrate the enclosure 102 and distribute treatments within the vacuum chamber 104. Examples of such treatments include ozone, gasses and mists applied by the donning system 100 before or as the article exits the vacuum chamber 104 on a body part of a user. In addition, or alternatively, lotions, powders and antimicrobials can be sprayed into the interior of the article via the ports 134 after the article has been inflated in the vacuum chamber 104 and before the body part of a user is inserted, or onto the body part of a user during insertion into the article.

Figure 2:
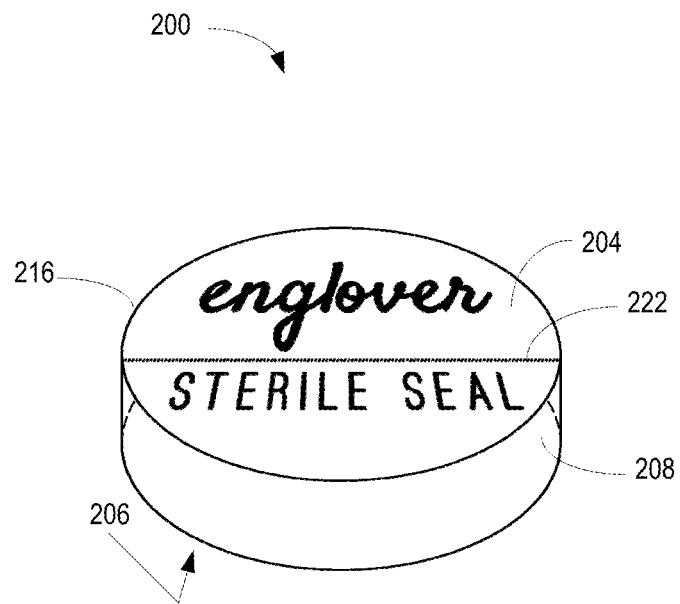
FIG. 2 is a perspective top view of an example sealed package.
Figure 3:
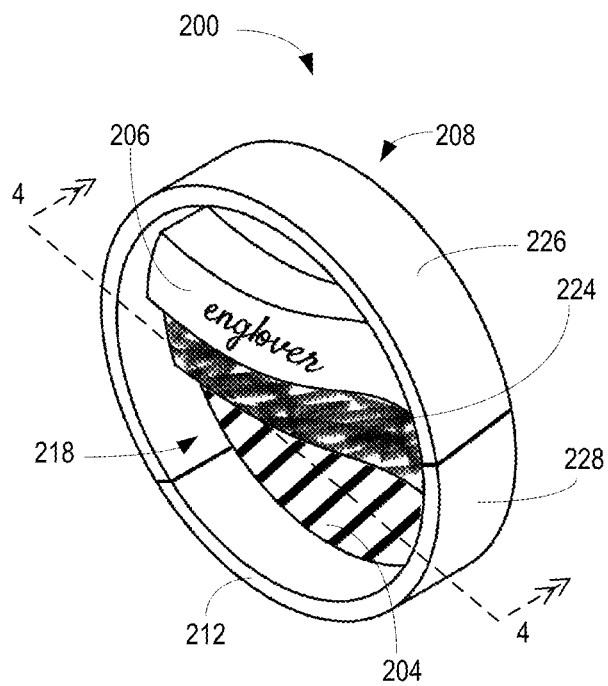
FIG. 3 is a perspective bottom view of an example of the sealed package of FIG. 2 with a portion of a barrier material and a portion of the wearable protective article removed for illustrative purposes.
Figure 4:
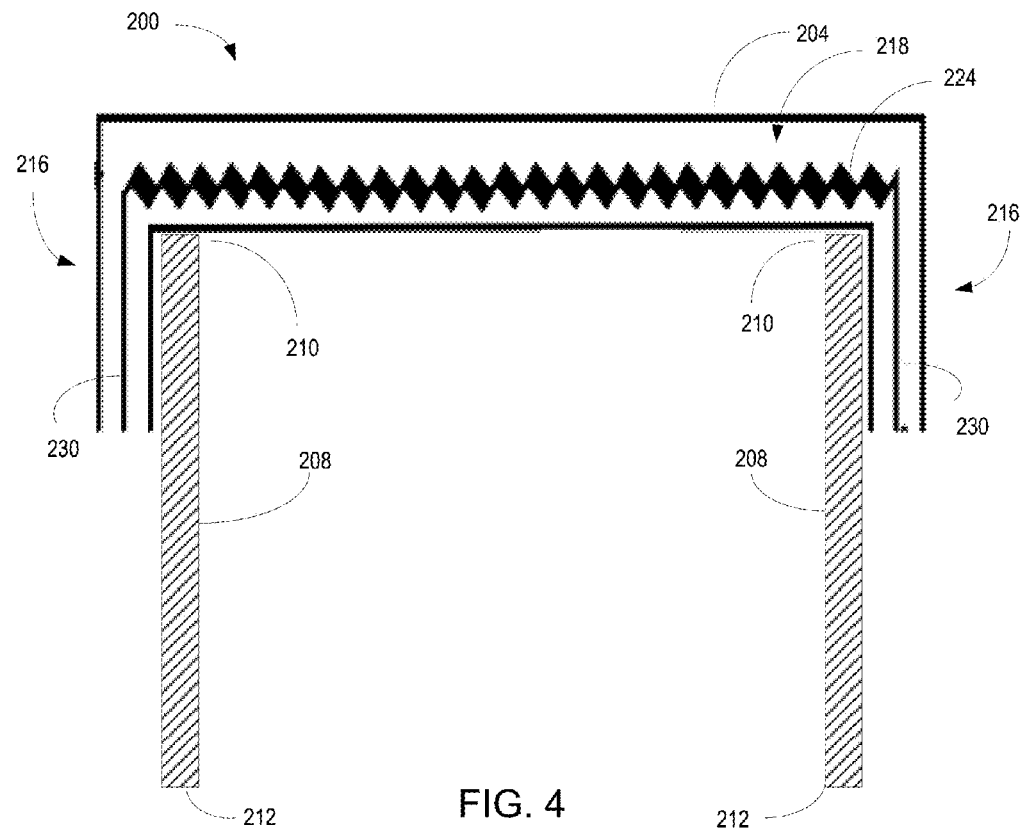
FIG. 4 illustrates a cross section view of an example of the sealed package of FIGS. 2 and 3.

FIG. 2 is a perspective top view of an example sealed package 200. FIG. 3 is a perspective bottom view of an example of the sealed package 200 of FIG. 2 with a portion of a barrier material and a portion of the wearable protective article removed for illustrative purposes. FIG. 4 illustrates a cross section view of an example of the sealed package of FIGS. 2 and 3.

Referring to FIGS. 2-4, the sealed package 202 may include a first barrier material 204, a second barrier material 206, and a member 208. The first barrier material 204 may form a top of the sealed package 200 and the second barrier material 206 may form a bottom of the sealed package 200. The member 208 forms a side wall of the sealed package 202 extending between a first end 210 of the member 208 and a second end 212 of the member 208. A peripheral edge 216 of the first barrier material 204 and the second barrier material 206 are each coupled with the first end 210 of the member 208 to form an enclosed cavity 218 between the first barrier material 204 and the second barrier material 206. The first barrier material 204 and the second barrier material 206 may be formed with a non-permeable, air tight, flexible, material coupled at the peripheral edge 214 to the member 208 to maintain the enclosed cavity 218 as a sterile environment.

Each of the first barrier material 204 and the second barrier material 206 may include a mechanical fuse 222, such as a seam. The mechanical fuse 222 may create an area of the first barrier material 204 and the second barrier material 206 that is designed to rupture at lower mechanical stress than the remainder of the first barrier material 204 and the second barrier material 206. In this way, the first barrier material 204 and the second barrier material 206 may rupture in a predictable fashion to provide ingress and egress to the enclosed cavity 218. For example, the second barrier material 206 may rupture to form a predetermined chute configured to direct the wearable protective article 224 away from an interior surface of the vacuum chamber 104 as the wearable protective article 224 expands into the vacuum chamber 104 due to being subject to a vacuum. In addition, the first barrier material 204 may rupture to create an aperture in the first barrier material 204 that is aligned with a throat of the wearable protective article 224.

A wearable protective article 224, such as a glove is illustrated in a compressed state in the enclosed cavity 218 formed by the combination of the first barrier material 204, the second barrier material 206. The member 208 may include a number of segments that are selectively separable away from one another. As best seen in the example of FIG. 3, the member 208 is illustrated as having a first segment 226 adjacent a second segment 228 that are arranged to form the sidewall as a ring structure. The sidewall extending away from the first end 210 to the second end 212 and formed to engage a device to movably separate the segments 226 and 228. The wearable protective article 224 may be releasably coupled to the segments 226 and 228. In other examples, additional segments may be included, and the member 208 may form other shapes, such as an ellipse, a square or a rectangle.

The peripheral edge 216 of the first barrier material 204 and the second barrier material 206 may be coupled at the first end 210 of the member 208, or extend around the first end 210 down the sidewall. The second barrier material 206 may be directly coupled with the member 208, and the wearable protective article 224 may be coupled to the member 208 by being coupled to the second barrier material 206. The first barrier material 204 may be coupled to the member 208 by being coupled to the wearable protective article 224. Although illustrated in FIG. 4 as separated, the peripheral edge 216 of the first barrier material 204 and the second barrier material 206, and a portion of a throat 230 are contiguously coupled to form an outer seal around the enclosed cavity 218.

In another example of the sealed package, the first barrier material may be coupled to the second barrier material at a peripheral edge of the first barrier material and the second barrier material to form an enclosed cavity between the first barrier material and the second barrier material. In this example, the member and the wearable protective article may be disposed in the enclosed cavity, with the member at least partially surrounding the wearable protective article. The enclosed cavity may be maintained as a sterile environment.

Figure 5:
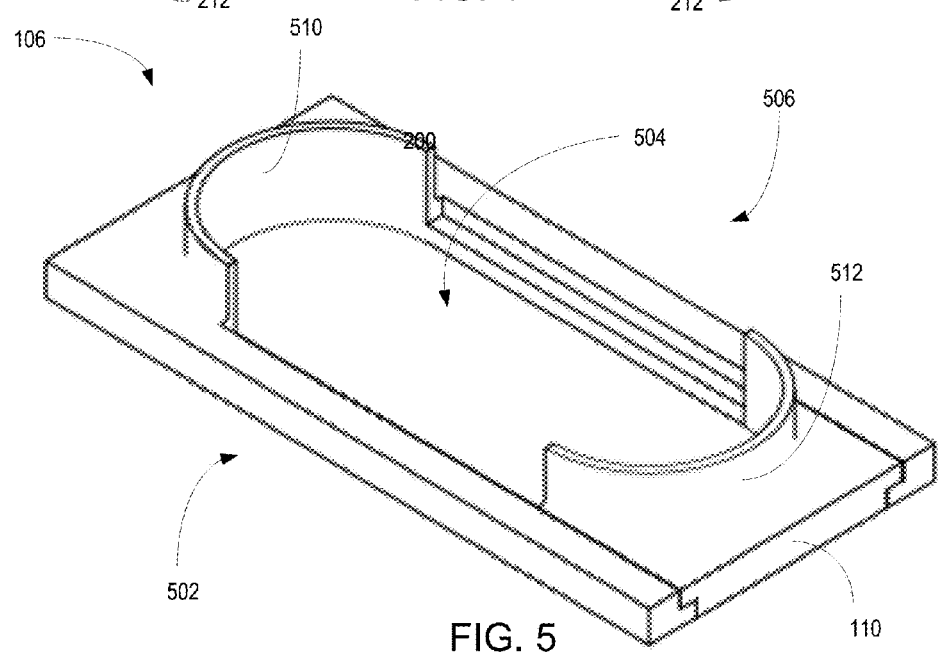
FIG. 5 is a perspective view of an example of a package mount included in the donning system.

FIG. 5 is a perspective view of an example of a package mount 106 included in the donning system 100. The package mount 106 includes the slidable member 110. In FIG. 5, the slidable member 110 is illustrated in an open position, whereas in FIG. 1, the slidable member 110 is illustrated in a closed position. The package mount 106 is formed with a body 502 that may be fixedly mounted to form a portion of the vacuum chamber 104 such that when the slidable member 110 is in the open position the only communication with the vacuum chamber 104 is via opening 504. The package mount 106 includes a collar 506 formed by a flange 510 on the base 502 and a flange 512 formed on the slidable member 110.

The flanges 510 and 512 are formed to receive the sidewall of the member 208 when the slidable member 110 is in the closed position such that the second end 212 of the member 208 encloses the flanges 510 and 512. The member 208 may contiguously align with the flanges such that the sealed package is frictionally maintained on the package mount 106. Once the member 208 is received on the package mount 106, the slidable member 110 may be slidable between the closed position and the open position to rupture the sealed package 200. The collar 506 is configured to grip the sealed package 112 via the member 208. The sealed package, and more specifically the first and second barrier materials, is removably coupled with the wearable protective article to provide a sterile barrier between the collar 506 and the wearable protective article while the wearable protective article is removably fixed to the collar 506. Since the wearable protective article is removably coupled with the sealed package, a throat in the wearable protective article is configured to expand to receive a body part of a user in response to the slidable member 110 transitioning from the closed position to the open position.

Figure 6:
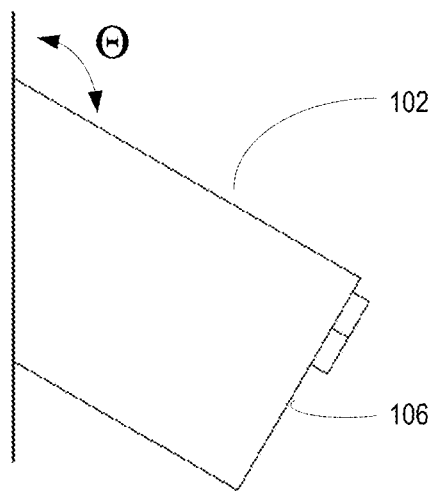
FIG. 6 is a side view of an example enclosure and package mount included in a donning system.
Figure 7:
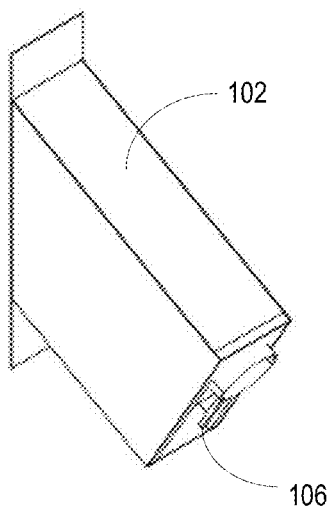
FIG. 7 is a perspective view of an example enclosure and package mount included in a donning system.
Figure 8:
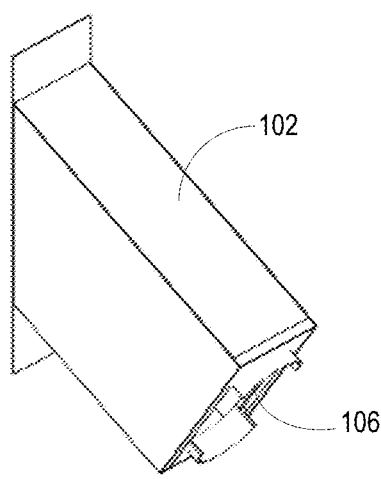
FIG. 8 is a perspective view of an example enclosure and package mount included in a donning system.

FIG. 6 is a side view of an example enclosure 102 and package mount 106 included in a donning system 100. The enclosure 102 may be mounted on a structure 602, such as a wall or article. The enclosure 102 may be mounted to provide a predetermined angle, such as 45 degrees, to allow a user to easily access the opening 504. For example, in a hospital setting, doctors preparing for a surgical operation may maintain their hands up after aseptically washing to avoid contamination and so that any materials on their arms do not run to their hands. FIG. 7 is a perspective view of an example enclosure 102 and package mount 106 included in a donning system 100. In FIG. 7, the package mount 106 is illustrated with the slidable member 110 in the closed position. FIG. 8 is a perspective view of an example enclosure and package mount included in a donning system in which the slidable member 110 is illustrated as being in the open position. Thus, a user may conveniently and readily access the enclosure 102 to obtain wearable protective article, such as surgical gloves.

Figure 9:
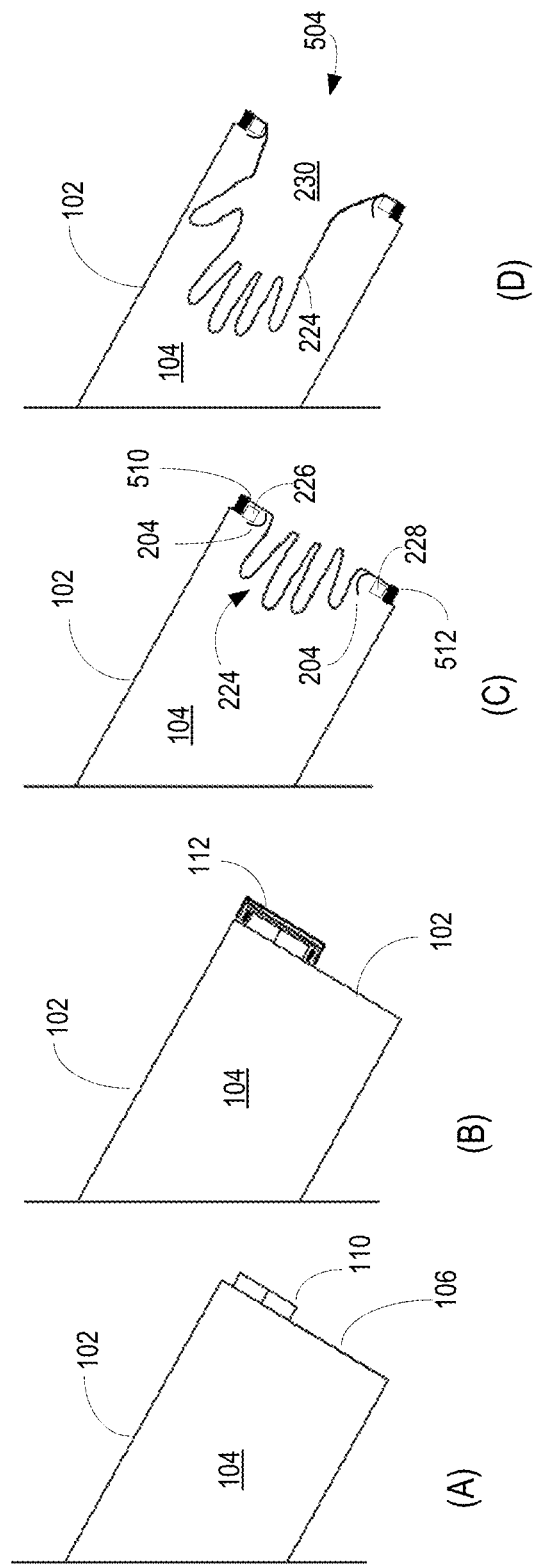
FIG. 9 illustrates an example of a sequence of operations of a donning system.

FIG. 9 illustrates an example of a sequence of operations of a donning system 100. In FIG. 9A, the operation is commenced with an enclosure 102 mounted at a predetermined angle and the slidable member 110 included on the package mount 106 in the closed position. In FIG. 9B, a sealed package is received on the package mount 106. In FIG. 9C, the slidable member 110 is slid from the closed position to the open position resulting in the flange 512 associated with the slidable member 110 being separated away from the stationary flange 510 associated with the base 502. As a result, the segments 226 and 228 are separated away from one another.

When the slidable member 110 is slid to the open position, the sealed package is ruptured by the segments 226 and 228, and the wearable protective article 224 is expanded into an expanded state by the vacuum within the vacuum chamber 104. More specifically, mechanical stress placed upon the mechanical fuse included in the second barrier material 204 by the segments 226 and 228 causes the mechanical fuse to actuate and the second barrier material 204 is ruptured in a predetermined area. Due to being exposed to the vacuum in the vacuum chamber 104 when the second barrier material 204 is ruptured, the wearable protective article 224 in the compressed state expands outward from the sealed package to the expanded state.

In FIG. 9D, the wearable protective article 224 is in the expanded state, and the opening 504 can receive a body part of a user, such as a hand, which can be extended through the expanded throat 230 of the wearable protective article 224. The vacuum chamber 104 is illustrated as being able to accommodate the wearable protective article expanded into the expanded state in the vacuum within the vacuum chamber 104 such that the wearable protective article 224 is space away from an interior surface of the vacuum chamber 104.

Although gloves are described, any other form of wearable protective article for donning of a portion of a user's body may be donned using the donning system 100. In the example of the articles being gloves, the sealed packages 112 containing the gloves may have the glove's thumbs pointing to a peak of a top segment 226 or 228 included in the member 208 so that when the wrist opening is extended and the glove is expanded the thumbs are in an up position, a natural orientation for the user to insert either hand. An elastomeric glove is typically made to fit either left or right hand, thumbs up is a natural orientation for either hand and allows the donning system 100 to be less complex than a different orientation for each hand, such as palms down were implemented.

Alternatively, if palms downward is preferred, the donning system may be configured in that orientation and the loading of the sealed packages may be rotated thumb right for the left hand and thumb left for the right hand. In either case, a separate vacuum chamber 104 and supporting functionality including two openings and two separate vacuum chambers to glove either hand or both simultaneously may be provided as needed.

The enclosure 102 is oriented with the opening 504 at a downward angle to allow the user to glove his hands as soon as possible while keeping, as is standard, elbows down, hands up position as long as possible after using antiseptic wash on the hands and arms. This is standard surgical room procedure to prevent antiseptic wash which has not dried from running back down the forearm and potentially recontaminating that area.

Powder is used in some gloves to make them easier to don. In 2011 the FDA advised against the use of powdered gloves for surgical and exam use because of concerns such as respiratory allergic reactions, rhinitis, conjunctivitis and dyspnea, respiratory problems, granuloma formation, and peritoneal adhesions. Powder free gloves have become the norm in healthcare since that time, however while manufacturers have sought changes in glove formulations to replace the functions of powder, there has not been a fully satisfactory replacement for many users. The glove donning system completely eliminates the problem that powder was used to solve. The glove is inflated greater than the size of the users hand so there is no friction or adhesion of the glove walls to overcome. Another frustration of air bubbles at the tips of the fingers is also no longer a problem, gloves collapse at the fingers first and the tips of the gloves are thus placed snugly against the tips of the fingers.

The wrists of gloves (throat) are not prestretched to accommodate the widest part of the hand in their packaging for two reasons—1) the elastomers that have been stretched out for a long period of time would not return fully to their original dimensions and 2) by not expanding the glove at manufacture or otherwise creating an expandable skirt that is part of the packaging and separates from the glove at donning, existing manufacturing does not require any modification. The packaging itself can be done at the end of a manufacturing stream or it can be done entirely post manufacture. Either one can be a fully automated process or use human intervention.

Many metal ions and other compounds exhibit abiotic characteristics that are enhanced when activated by specific wavelengths of UV light. This characteristic varies in intensity and duration by compound and environmental conditions, but in most cases can be reactivated numerous times. Predetermined formulations of materials used to form the articles, such as gloves donned using the donning system 100 can be used to take full advantage of this property as well as the antimicrobial effect of UV by itself when applied by the donning system 100. The donning system 100 can also take advantage of this effect with the materials used and the reach of the UV radiation to keep the machinery included in the system itself sterile. Bulbs or UV LEDs can be positioned to expose all of the article, such as a glove. Mirrors may also be used to fully immerse the article in ultraviolet rays. The donning system 100 will also block UV rays from escaping in order to shield and to protect the eyes of the user, In addition, in donning systems where a UV light source produces a wavelength and/or intensity of UV light that may harm human skin, the donning system 100 may be formed and designed to not allow exposure of human skin.

In addition, or alternatively, disinfecting gases may be used within the donning system 100 to treat articles. For example, after the hand of a user is inserted into an article such as a glove, one or more ports in the walls of the vacuum chamber can relieve the vacuum by injection of such gases.

Aerosols such as mists or sprays of antiseptics, antimicrobial enzyme solutions, antibiotics, antivirals and antifungals can all be sprayed onto the outer surface of the article by the donning system 100 as part of the automated donning process In an example system that includes a rigid wall vacuum chamber machine, these aerosols can be released through ports pointing at the article and sprayed into the vacuum and onto the article before the wearers body part upon which the article was installed is removed. In other examples, application of such aerosols by the donning system 100 may occur before the body part of the use is inserted. Indicator chemistry may also be applied to the outer surface of the article. These indicators may detect pH, the presence of protein compounds, the presence of coliform or other bacteria, specific viruses or virus families, the presence of explosive materials or any other environmental contaminants of concern.

FIG. 10 is an exploded view of an example donning system 1000. In this example, the donning system 1000 may include an expandable body 1002, such as bellows packaging. The expandable body 1002 may form a perimeter around an enclosed cavity 1003 that may be transitioned from a compressed cavity state to an expanded cavity state. An example of a compressed cavity state is illustrated by the relatively small enclosed cavity 1003 illustrated in FIG. 10. FIG. 11 is a cutaway side view of an example donning system. In FIG. 11, an example of an expanded cavity state is illustrated within the expandable body 1002 by the relatively large enclosed cavity 1003 depicted.

Referring to FIGS. 10 and 11, the expandable body 1002 includes a rim 1004 defining an opening in the expandable body 1002 to provide access to the enclosed cavity 1003. A wearable protective article 224 may be removably coupled with the rim 1004 and may be disposed in the enclosed cavity 1003. A throat 230 of the wearable protective article 224 may be in an open position within the rim 1004. A cover 1006 may be removable engaged with the rim 1004 to span the opening and seal the wearable protective article 224 in the enclosed cavity 1003.

FIG. 12 is a perspective view of an example tool 1200 for the donning system 1000 of FIGS. 10 and 11. The tool 1200 may be inserted under the rim 1004 of the expandable body 1002 by a user. The user may grasp the tool 1200 and a handle 1008, such as a ring that may be included at an end of the expandable body 1002 opposite the rim 1004. After manually removing the cover 1006, the user may manually move the tool 1200 and the handle 1008 in opposite directions to transition the expandable body 1002 from the compressed cavity state to the expanded cavity state. The expandable body 1002 may create a vacuum in the enclosed cavity 1003 by expansion from the compressed cavity state to the expanded cavity state.

The wearable protective article 224 may expand into the expanded enclosed cavity 1003 due to the vacuum as illustrated in FIG. 11. The throat 230 of the wearable protective article 224 may be exposed when the cover 1006 is removed. The throat 230 may be coupled with the rim 1004 and is sized to receive the body part of the user. The rim 1004 is similarly sized to accommodate a body part of a user. The wearable protective article 224 may remain positioned in the enclosed cavity absent contact with the interior surface of the expandable body 1002 in either the compressed cavity state or the expanded cavity state so as to avoid contamination. Alternatively, or in addition, the interior of the article may be a sterile before removal of the cover 1006, the exterior of the article and the interior of the expandable body 1002 (bellows packaging) may maintain sterility until the wearable protective article 224 is separated from the expandable body 1002.

In some examples, the donning system 1000 may also include a barrier material 1010 between the enclosed cavity 1003 and the wearable protective article 224. The barrier material 1010 may be coupled with the rim 1004 and spanning the opening adjacent the cover 1006 so that a cavity is formed between the cover 1006 and the barrier material in which the wearable protective article 224 is disposed. This barrier material might separate the wearable protective article 224 from a treatment until the wearable protective article 224 is ready to be donned. Alternatively, or in addition, the wearable protective article 224 may be maintained in a sterile environment in the cavity formed. The barrier material may include a mechanical fuse 1012. The mechanical fuse 1012 may rupture a predetermined area of the barrier material in response to the vacuum created exceeding a predetermined mechanical stress on the mechanical fuse so that the wearable protective article 224 expands into the expanded enclosed cavity 1003 in the expanded state without contacting an interior surface of the expandable body 1002.

In this example configuration, the outside of the article can be treated using capsules or other reservoirs of liquid or gas that the donning system 1000 can control to release their contents as the bellows is opened and/or when the vacuum is released. The donning system 1000 may include a treatment system 1012. The vacuum around the article can be released with a predetermined gas from the treatment system, such as an air mixture rich in ozone (O3), or O3 can be circulated or generated in the negative pressure air around the glove to operate as a disinfectant.

Personal protection of emergency and medical workers is often the primary reason for articles such as gloves and other garments and is always at least a secondary concern. The donning system 100 can also enhance the protection that the article, such as a glove or other garment, gives to the side facing the body of a wearer effectively by treating before the user puts the article on. This may be accomplished via spray ports included in the treatment system 1012. The ports may located in the system 1000 near the throat 230 of the machine pointing toward the interior of the article, such at once the article is open and ready to receive the body part of a wearer, the spray ports may be initiated to disinfect the interior surfaces of the article. Indicator chemistry may also be introduced into the article to alert the user during the use of or on disposal of the article that it was breached and is contaminated or potentially contaminated. A breach indicator may be as simple as a dry pigment or dye that will show within or outside the garment when exposed to any liquid.

Alternatively, or in addition, such spray ports may be positioned to direct a liquid or gas toward the body part of the wearer, such that when the wearer is preparing to put on the article the wearers body part is disinfected or an indicator is applied to that body part. For example, as a wearer is putting on gloves, ports facing the users' hands such that the hands are disinfected just prior to entering a glove.

Individual packaging of gloves and other articles, such as condoms, which can be used with the donning system 100 can be made so that the packaging itself creates the vacuum to the outer surface of the article as the package itself is extended accordion or bellows fashion.

Long cuffed gloves are the glove of choice for most Ebola and other hazardous workers. Long cuffed gloves are usually not snug at the cuff because to make them so would add to the difficulty of putting them on and make them much more likely to tear. The donning system 100 can make it easy to put on long elastomeric gloves farther up the forearm and even sleeves past the biceps. Because the current gloves leave a dangerous gap which can quickly fill with a patient's body fluids in the field they are often taped at the cuff and sometimes to a protective suit.

Figure 13:
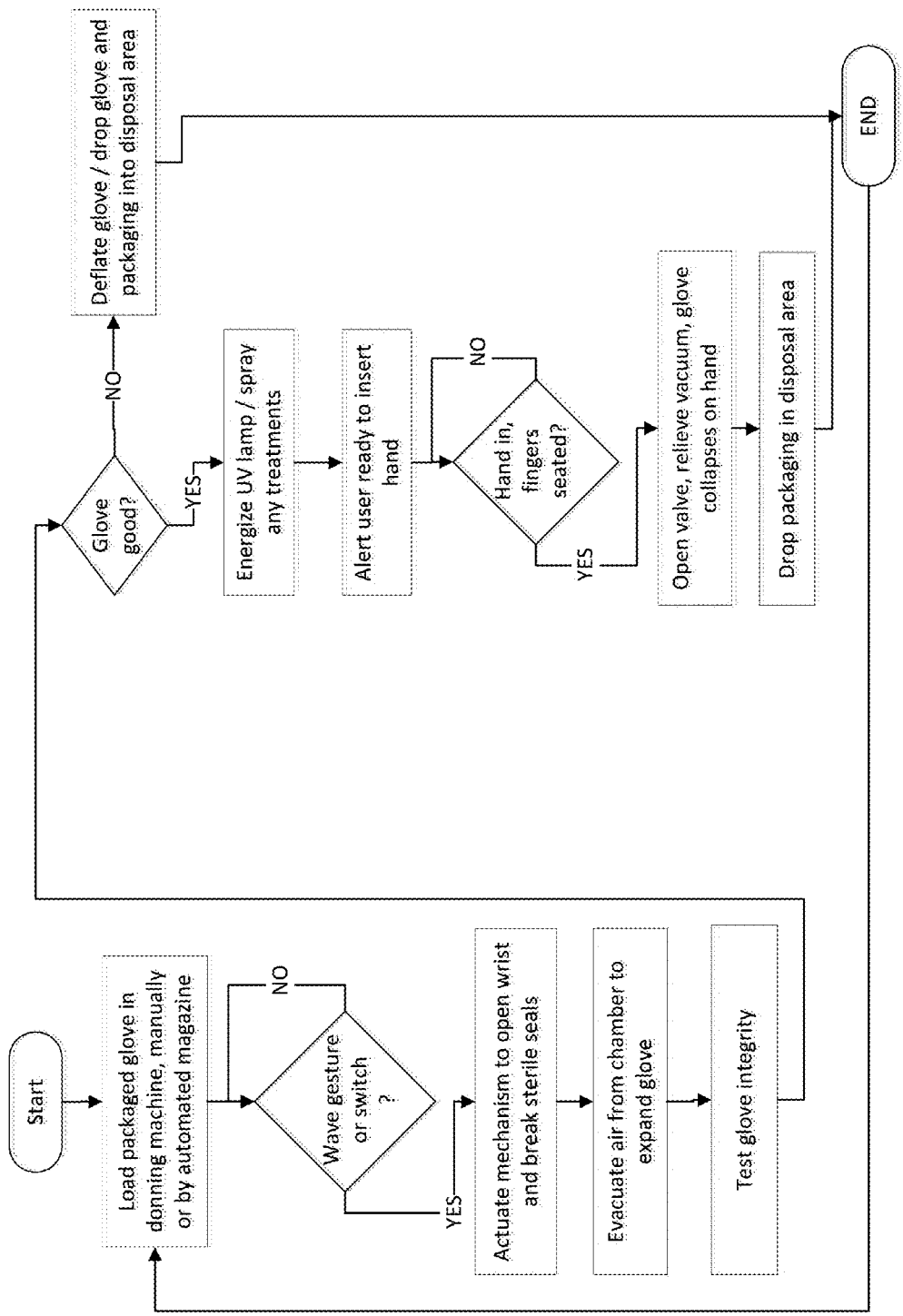
FIG. 13 is a flowchart of an example of operation of the donning system.

FIG. 13 is a flowchart of an example of operation of the donning system to provide donning of an article by a user. The donning system 100 can provide for automated donning of any article using the processor. For example, footwear such as booties, socks, stockings or boots are needed in medical care, agriculture, sewage and sanitation, clean room and other fields. Such articles are notoriously hard for a user to put on, and often create more contamination issues than they solve. The donning system 100 can make it easy for someone to step into any of these articles. In addition, pants, hose and/or waders processed by the donning system 100 could be very helpful for someone exposed to toxic or contaminated liquid material, such as contaminated waters.

The donning system 100 may also be used for other articles, such as shirts or coats.

In an example, nitrile rubber can make an excellent protective skull cap or hood. A hood might incorporate windows for the eyes and air filtration for breathing and breathing protection. In another example, full body suits may be used. In this example, the full body suits may be used instead of, or in addition to, Tyvek suits.

In another example, the articles may be condoms or condom catheters. The self-contained bellows packaging performed by the donning system 100 seems to be the ideal means to package either a condom or a condom catheter. Because a condom catheter generally cannot be placed on a patient without considerable difficulty and some discomfort and still be snug enough to prevent leakage the donning system 100 could become the preferred condom catheter for most healthcare.

The methods, devices, processing, circuitry, and logic described above may be implemented in many different ways and in many different combinations of hardware and software. For example, all or parts of the implementations may be circuitry that includes an instruction processor, such as a Central Processing Unit (CPU), microcontroller, or a microprocessor; or as an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples.

Accordingly, the circuitry may store or access instructions for execution, or may implement its functionality in hardware alone. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed. For instance, the circuitry may include multiple distinct system components, such as multiple processors and memories, and may span multiple distributed processing systems. Parameters, databases, and other data structures may be separately stored and managed, may be incorporated into a single memory or database, may be logically and physically organized in many different ways, and may be implemented in many different ways. Example implementations include linked lists, program variables, hash tables, arrays, records (e.g., database records), objects, and implicit storage mechanisms. Instructions may form parts (e.g., subroutines or other code sections) of a single program, may form multiple separate programs, may be distributed across multiple memories and processors, and may be implemented in many different ways. Example implementations include stand-alone programs, and as part of a library, such as a shared library like a Dynamic Link Library (DLL). The library, for example, may contain shared data and one or more shared programs that include instructions that perform any of the processing described above or illustrated in the drawings, when executed by the circuitry.

While various embodiments have been described, it will be apparent to those of ordinary skill in the art that many more embodiments and implementations are possible. Accordingly, the embodiments described herein are examples, not the only possible embodiments and implementations.

I claim:

1. A system comprising:
an enclosure formed as a vacuum chamber; and
a package mount forming a portion of the vacuum chamber, the package mount comprising a slidable member configured to receive a sealed package containing a wearable protective article in a compressed state;
the slidable member slidable between a closed position and an open position to rupture the sealed package, and the enclosure configured to accommodate the wearable protective article in an expanded state within the vacuum chamber such that the wearable protective article is entirely spaced away from an interior surface of the vacuum chamber.

2. The system of claim 1, wherein the slidable member is slidable between a closed position and an open position to rupture the sealed package, and the enclosure configured to accommodate the wearable protective article expanded into an expanded state in a vacuum within the vacuum chamber such that the wearable protective article is space away from an interior surface of the vacuum chamber.

3. The system of claim 1, wherein the package mount comprises a collar on which the sealed package is mounted, the collar formed with a flange on the slidable member configured to separate away in the open position to cause the sealed package to rupture.

4. The system of claim 1, wherein the wearable protective article is expandable out of the seal package to the expanded state in response to a vacuum being present in the vacuum chamber.

5. The system of claim 1, wherein the wearable protective article is configured to receive and accommodate a body part of a user while in the expanded state.

6. The system of claim 1, wherein the sealed package is configured to rupture to expose the wearable protective article to a vacuum present in the vacuum chamber.

7. The system of claim 1, wherein the collar is configured to grip the sealed package, and the sealed package is removably coupled with the wearable protective article to provide a sterile barrier between the collar and the wearable protective article while the wearable protective article is removably fixed to the collar.

8. The system of claim 1, wherein the wearable protective article is removably coupled with the sealed package such that a throat in the wearable protective article is configured to expand to receive a body part of a user in response to the slidable member transitioning from the closed position to the open position.

9. A system comprising:
a first barrier material;
a second barrier material coupled to the first barrier material at a peripheral edge of the first barrier material and the second barrier material to form an enclosed cavity between the first barrier material and the second barrier material;
a member coupled with the peripheral edge of the first barrier material and the second barrier material, the member comprising a plurality of segments that are selectively separable away from one another; and
a wearable protective article disposed in the enclosed cavity and releaseably coupled with the segments.

10. The system of claim 9, wherein the plurality of segments are arranged to form a ring structure that includes a first edge to which the peripheral edge of the first barrier material and the second barrier material are coupled and a side wall extending away from the first edge to a second edge positioned away from the peripheral edge of the first barrier material and the second barrier material.

11. The system of claim 9, wherein the first barrier material and the second barrier material comprise a non-permeable, air tight, flexible, material coupled at the peripheral edge to maintain the enclosed cavity as a sterile environment.

12. The system of claim 9, wherein the segments include a sidewall formed to engage a device that is movable to separate the segments away from one another.

13. The system of claim 9, wherein the first barrier material and the second barrier material each being configured to include a mechanical fuse, the mechanical fuse configured to rupture a predetermined area of the first barrier material and the second barrier material in response to application of a predetermined level of mechanical stress to the first barrier material and the second barrier material.

14. The system of claim 13, wherein selective separation of the segments applies the predetermined level of mechanical stress.

15. The system of claim 9, wherein the member is configured to receive a body part of a user to engage the wearable protective article when the segments are selectively separated.

16. The system of claim 15, wherein the wearable protective article includes a throat coupled with the segments, the throat transitioned from a closed position to an open position to receive the body part of the user in response to the segments being selectively separated.

17. A donning system comprising:
an enclosure formed as a vacuum chamber;
a package mount forming a portion of the vacuum chamber; and
an ultraviolet (UV) light source;
the package mount comprising a member to receive and rupture a sealed package containing an abiotically treated wearable protective article in a compressed state, and
the vacuum chamber formed to accommodate the abiotically treated wearable protective article in an expanded state entirely spaced away from an interior surface of the vacuum chamber and positioned for exposure to UV light emitted by the UV light source.

18. The system of claim 17, wherein the UV light source is positioned to photoactivate an abiotic surface of the abiotically treated wearable protective article.

19. The system of claim 17, further comprising at least one spray port disposed in the enclosure to apply a germicidal agent on an outer surface of the abiotically treated wearable protective article.

20. The system of claim 17, wherein the at least one spray port is positioned to apply an indicator chemistry to a surface of the abiotically treated wearable protective article.

21. The system of claim 9, wherein the article includes an abiotic layer, the abiotic layer comprising at least one of titanium dioxide ($TiO_2$) or silver (Ag).

22. The system of claim 1, further comprising an ultraviolet (UV) light source positioned in the enclosure to activate an abiotic layer on the wearable protective article with UV light emitted from the UV light source.

* * * * *